United States Patent [19]

Ulrich

[11] Patent Number: 5,569,304
[45] Date of Patent: Oct. 29, 1996

[54] APPARATUS FOR INDUCING BLOODLESSNESS AT THE EXTREMITIES OF A PATIENT

[76] Inventor: Heinrich C. Ulrich, Buchbrunnenweg 12, 89081 Ulm, Germany

[21] Appl. No.: 242,734

[22] Filed: May 13, 1994

[30] Foreign Application Priority Data

May 27, 1993 [DE] Germany .......................... 43 17 600.3

[51] Int. Cl.$^6$ ...................................................... A61B 5/00
[52] U.S. Cl. ............................................ 606/201; 128/679
[58] Field of Search ......................................... 606/201–203; 128/679, 680, 681, 686, 96.1, 118.1, 774, 784; 602/62, 67

[56] References Cited

U.S. PATENT DOCUMENTS

| 4,321,919 | 3/1982 | Lemelson et al. | 606/202 |
| 4,520,819 | 6/1985 | Birmingham et al. | 606/202 |
| 4,605,010 | 8/1986 | McEwen | 606/202 |
| 4,671,290 | 6/1987 | Miller et al. | 128/681 |
| 4,770,175 | 9/1988 | McEwen | 606/203 |
| 5,048,536 | 9/1991 | McEwen | 128/748 |
| 5,112,347 | 5/1992 | Tahari | 606/200 |
| 5,181,522 | 1/1993 | McEwen | 128/748 |
| 5,307,811 | 5/1994 | Sigwart et al. | 128/677 |
| 5,383,893 | 1/1995 | Daneshvar | 606/201 |

*Primary Examiner*—Michael Powell Buiz
*Assistant Examiner*—Nancy Mulcare
*Attorney, Agent, or Firm*—Herbert Dubno

[57] ABSTRACT

A compression apparatus for synthetic induction of bloodlessness at an extremity of the patient or for intravenous local anesthesia can have automatic blood pressure measurement controlling a microprocessor which regulates the valve leading to the compression sleeve automatically. Upon a failure of the automatic control system, a manual pressure control valve is brought into play and allows manual adjustment of the compression pressure in the sleeve.

11 Claims, 2 Drawing Sheets

5,569,304

APPARATUS FOR INDUCING BLOODLESSNESS AT THE EXTREMITIES OF A PATIENT

FIELD OF THE INVENTION

My present invention relates to a compression apparatus for inducing a synthetic state of bloodlessness at the extremities of a patient, usually for surgical intervention or for intravenous local anesthesia. More particularly the invention relates to an apparatus for these purposes which comprises a compression sleeve adapted to be placed around the extremity and pressurizable through a controllable pressure-regulating valve with a pressure medium capable of establishing a compression level in the sleeve which will induce a synthetic state of bloodlessness at the extremity for surgical intervention or intravenous local anesthesia.

BACKGROUND OF THE INVENTION

A compression apparatus of the aforedescribed type can be used in medicinal practice for the creation of a synthetic state of bloodlessness as an incident to some surgical intervention at the extremity which requires that the flow of blood to the extremity be interdicted. The apparatus is applicable to upper and lower extremities and may utilize a so-called double-chamber sleeve which is suitable also for intravenous local anesthesia. The compression pressure within the sleeve, therefore, is intended to prevent the incursion of blood to portions of the extremity distal to the compression sleeve for the duration of the surgical procedure or operation. The compression pressure level is generally within a certain range in conventional apparatus of this type with the disadvantage that from time to time an excessive pressure may be applied. Excessive pressures can result in the formation of lesions, pressure-induced weakening of the limb, and later onset of disorders.

OBJECTS OF THE INVENTION

It is the principal object of the present invention, therefore, to provide an improved compression apparatus of the type previously described which can prevent overstepping of limiting values of the compression pressure and the detrimental effects which might be associated therewith, including the formation of lesions and weakening of the treated region.

Another object of this invention is to provide an improved compression apparatus for synthetically generating a state of bloodlessness distal to the compression sleeve or for intravenous local anesthesia, whereby the compressive force applied to the sleeve to the extremity does not exceed safe values and dangers encountered with earlier systems are obviated.

Still another object of this invention is to provide an improved compression apparatus which is easier to handle, is safer to use and is more readily controlled than earlier apparatus and which can be used for both upper and lower extremities and for any purpose for which exclusion of blood from the extremities distal to the compression sleeve is desired.

SUMMARY OF THE INVENTION

These objects and others will become apparent hereinafter are attained, in accordance with the invention utilizing an automatic blood-pressure measuring unit and a control-signal generator which determines continuously or at controllable time intervals, periodically-measured values of the blood pressure and produces control signals in response to these measured values for controlling a pressure-control value so that the compression pressure in the compression sleeve is varied correspondingly to the change in measured blood pressure and in step therewith.

More particularly, an apparatus for inducing bloodlessness in an extremity of a patient for a surgical procedure or for intravenous local anesthesia can comprise:

a source of a gas under pressure;

a compression sleeve adapted to surround the extremity and connectable with the source for pressurization thereby to compress the extremity;

a controllable pressure regulating valve between the source and the sleeve for regulation a gas pressure in the sleeve;

an automatic blood pressure measuring device for monitoring blood pressure of the patient at least intermittently and producing a signal representing measured blood pressure; and a control signal generator connected to the automatic blood pressure measuring device and to the controllable pressure regulating valve for receiving the signal representing measured blood pressure and producing a control signal operating the valve to alter pressure in the sleeve in response to a change in measured blood pressure.

The invention provides an automatic matching of the compression pressure during the operation to the changing blood-pressure value which occurs during surgery. If the blood pressure of the patient which is measured continuously or periodically during the surgical intervention increases or falls, the measured value will correspondingly change and the control signal fed to the valve will vary correspondingly so that the compression pressure in the sleeve will also alter correspondingly so that excessive compression pressure and the detrimental effects thereof on the patient can no longer arise.

In a preferred embodiment of the invention, the transformation of the measured blood pressure into the control signal for the pressure-control valve is so effected that the compression pressure in the sleeve is increased by an amount exactly equal to the increase in actual measurement of the blood pressure or the compression pressure in the sleeve is made equal to the actual measured blood pressure plus a predetermined additional pressure.

In the simplest case, the additional pressure has a constant value independent of the actual measured blood pressure or the measured value to which the pressure-control valve responds. However, it is also within the scope of the invention to have the additional pressure be variable and selected in dependence upon the actual measured blood pressure.

The transformation of the blood-pressure value into the control signal for the pressure-control valve can be effected in various ways. Preferably the control-signal generator is integrated in a computer-supported control unit and a microprocessor determines the control signal value from the magnitude of the measured blood pressure.

For safety reasons it has been found to be advantageous to provide parallel to the automatic pressure control valve which is operated by the control-signal generator, a hand-adjustable pressure-control valve. The compression sleeve can be switched over between both of these pressure-control valves via a two-way valve.

Should blood-pressure-dependent control of the first pressure-control valve via the control-signal generator fail for some reason or it is desired to cut out this automatic valve, the manual mechanically-actuatable pressure relief valve can be automatically switched in so that the compression pressure in the sleeve will not exceed or fall below predetermined levels to create dangerous or injurious conditions.

According to a feature of the invention, a pressure sensor is provided to detect the compression pressure and a switching of the compression sleeve to the hand-operated pressure control valve is enabled as soon as or as long as the compression pressure (actual value or measured value) measured by the pressure sensor deviates from the compression pressure determined by the blood-pressure measurement (setpoint value of the compression pressure).

In addition or alternatively, this pressure sensor can operate an alarm. Advantageously, the comparison of the actual value and the setpoint value is effected in the control unit which automatically switches over the two-way valve when the measured value deviates from the setpoint value by a relatively small tolerance.

The apparatus or device of the invention can include display or indicator means for the measured value of the blood pressure, the additional pressure and/or the setpoint value of the compression pressure, and data input means for setting the desired additional pressure. The compression sleeve may also be connected to a manometer showing the compression pressure (measured value).

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
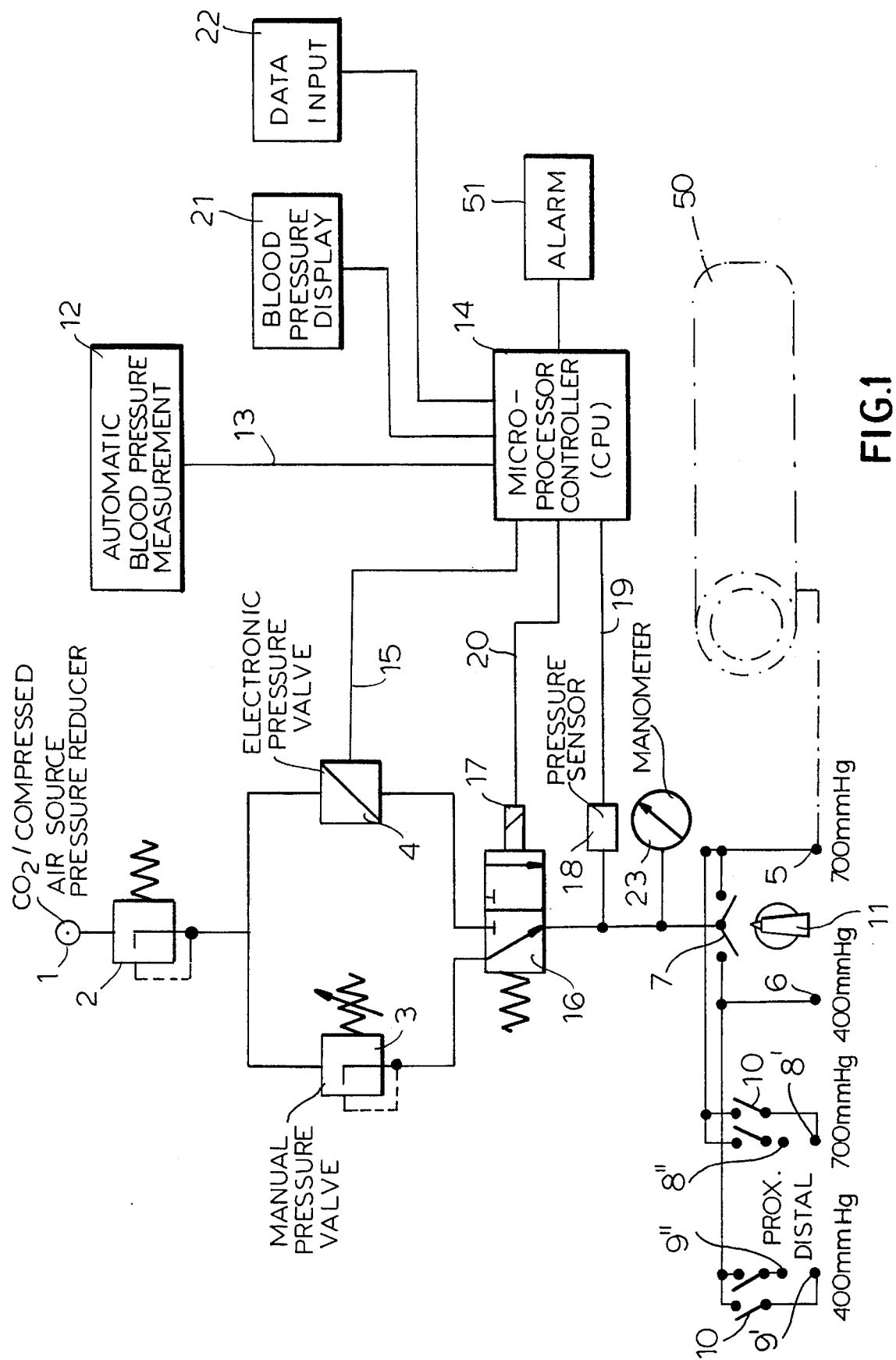
FIG. 1 is a block diagram illustrating both electronic and fluid paths of a compression apparatus according to the invention.

The compression apparatus shown in FIG. 1 comprises a source 1 of a pressurizing medium, usually a gas, which can be a central compressed-air-supply system, a compressor, a tank of compressed gas, such as a $CO_2$ bottle provided with a pressure-reducing valve, or the like.

A pressure reducer connected to the source 1 reduces the supply pressure to a pressure suitable for the compression apparatus, generally between 2 and 5 bar. A further pressure reduction can be effected in the steplessly-adjustable-pressure control valves 3 and 4 whose output pressures, depending upon the setting or adjustment of the respective valve can be between 0 and 700 mm Hg.

At connectors 5 and 6, e.g. quick-connect or disconnect connectors, a compression sleeve 50 can be connected to the pressurization system. The compression sleeve may be of the type described in German Patent document DE 33 33 311. The connector 5 is provided to deliver a maximum pressure of 700 mm Hg and the compression sleeve is connected to it when it is to be applied to a lower extremity. The other connector 6 is limited to a pressure value of 400 mm Hg so that it is used when the sleeve is to be applied to an upper extremity.

A mechanical valve 7 is provided for switching over the pressurizing system between the connectors 5 and 6. Utilizing connectors 8, 8' and 9, 9', with selector valves 10, double-chamber compression sleeves can be hooked up as can be used in intravenous local anesthesia. A double-chamber sleeve has proximal and distal pressure chambers so that the connectors 8', 9' can be used for the distal chamber and connectors 8", 9" for the proximal chamber The connectors 8', 8" are used when the compression pressure should reach 700 mm Hg while the connectors 9, 9' are used for compression pressures up to 400 mm Hg.

The valve 7 may be operated by a handle having the respective switchover positions.

The apparatus shown in FIG. 1 also comprises an automatic blood-pressure-measuring device 12 that can provide a continuous measurement of the blood pressure of the patient or can provide blood pressure measurement readings periodically, e.g. every 3 to 5 minutes.

The blood pressure measurement is supplied via the signal line 13 to a microprocessor-based controller 14 or some other microcomputer which can include a control-signal generator. The control signal is outputted by the control unit 14 applied at 15 to the electronically-operated pressure control valve 4.

The blood-pressure-dependent control of valve 4 ensures that the compression pressure in the sleeve 50 will be changed correspondingly to a change in the measured blood pressure. If the blood pressure of the patient rises, the compression pressure is raised and vice versa. In the simplest case, the transformation of the blood-pressure-measurement signal from the blood-pressure-measurement unit 12 into the control signal outputted by the controller 14 to the pressure-control valve 4 is so effected that the compression pressure is increased from the actual measured blood pressure by a predetermined additional pressure so that the compression pressure when blockage of the blood flow to the extremity is desired, is always a fixed amount greater than the actual measured blood pressure. The microprocessor controller 14 is programmed to calculate the requisite control-signal amplitude from the value of the measured blood pressure.

The hand-operated valve 3 is also a pressure-regulating valve. The microprocessor controller 14 has an output 20 which is applied to the magnetic effector 17 of a two-way valve 16 selectively connecting the pressure-regulating valves 3 and 4 with the valve 7 which can connect the pressure to the respective connector 5 or 6.

The compression pressure within the sleeve 50 is measured by a pressure sensor 18. When the pressure sensor 18 measures a compression pressure which deviates from a setpoint value determined by the blood pressure measurement from the desired pressure in the compression sleeve, the valve 16 is switched over automatically to cause the manual valve 3 to be effective.

The output of the pressure sensor 18 and the control input of the valve 16 can connect via lines 19 and 20 with the control unit 14. A comparison of the measured value of the compression pressure with the setpoint value thereof is effected in the control unit 14 which then switches the valve 16 as is necessary via control line 20 when the measured and setpoint values deviate excessively. An alarm 51 can also be triggered by the comparison of this measured value with the actual value.

The control unit 14 is also provided, as is apparent from FIG. 1 with a display 21 for the measured-blood-pressure value, the additional pressure, the setpoint of the compression pressure and any other magnitudes which may be of interest. The processor 14 has a data input unit 22, for example, a keyboard, which can introduce the value of the additional pressure and can be used as desired to program the microprocessor. A manometer showing the compression pressure in the sleeve is represented at 23.

Figure 2:
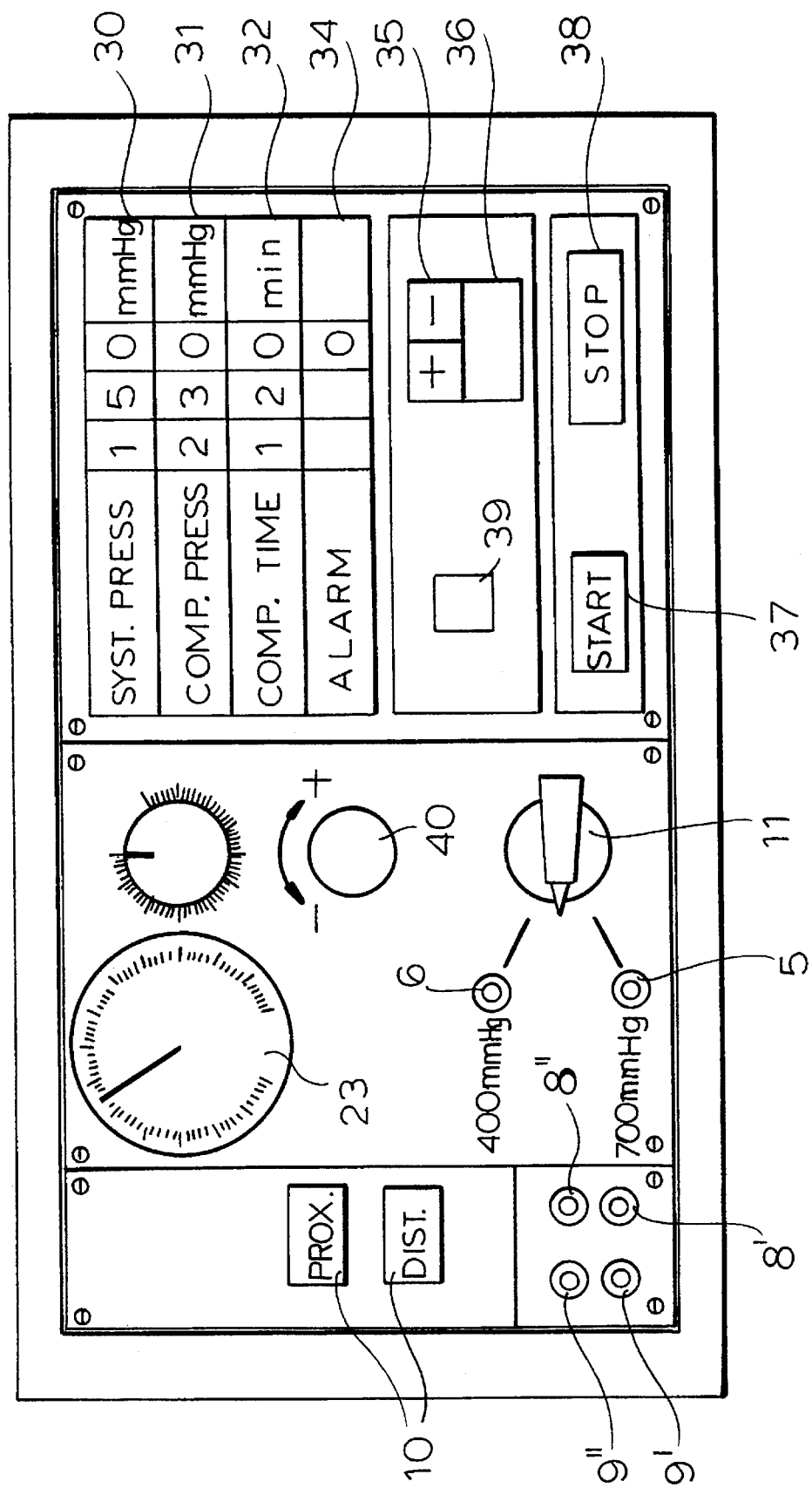
FIG. 2 is an elevational view of the display and indicator parts of the compression apparatus of FIG. 1.

Pressure control is effected by the unit 14 by adding the additional pressure to the measured systolic blood pressure and the generation in the compression sleeve of the resulting sum. The setpoint is maintained at this desired compression pressure. If necessary, the additional pressure can be varied by manual input to the controller 14. For the duration of the surgery, the control unit 14 effects electronic monitoring of all relevant parameters. In the case of failure, optical and acoustical alarms are triggered and in an error-display field 34 of the apparatus (FIG. 2), a code number is displayed which indicates the nature of the error. If it is not possible to eliminate the error in a reasonable time in the apparatus, the compression pressure is relieved or the two-way valve 16 switches over automatically from the automatic valve 12 to the manual valve 3.

Upon switching on of the apparatus, all of the fields 30-34 or rather all of the values displayed in these fields, flash. This represents a test of the indicators and can be terminated by depressing one of the plus or minus buttons 35 or the actuating button 36. In the display field 30, the systolic blood pressure is displayed. In the display field 31 the additional pressure is displayed together with the compression sleeve pressure as the setpoint value. The additional pressure can be raised or lowered by actuating the plus or minus buttons 35 and set by actuating the button 36. The pressure actually generated within the sleeve can also be displayed as is, in field 32, the duration for which the compression pressure is applied.

The measured value determined by the sensor 18 as a rule deviates from the setpoint value used to control the valve 4 and this deviation can be displayed in the field 34 as an error. For example, in this field, the number 2 can be displayed when the pressure is too low while the number 3 is displayed when the pressure is too high. In these cases, the compression pressure is adjusted by manual operation of the handle 40 of the pressure-control valve 3 until the illuminated error field 34 is extinguished. The pressure value displayed by the manometer 23 is then equal to the mean compression pressure.

The automatic operation is initiated by pressing the start button 37 and the operation is terminated by pressing the stop button 38.

When the start button is depressed, the two-way valve 16 connects the pressure-control valve 4 in the path of the compression sleeve and thus ensures automatic control of the compression pressure in accordance with systolic blood pressure. The systolic blood pressure is then displayed in field 30 while in field 31 the setpoint value of the compression pressure is displayed and field 32 displays the compression time while field 34 indicates any possible error. To cut off the automatic operation, the button 38 is depressed.

The valve 16 returns to the position shown in FIG. 1 and the manual valve 3 is rendered effective. By actuation of the handle 30 for this valve, the pressure can be vented until the pressure in the sleeve 50 falls slowly to zero. Upon failure to the electronic system, the device can be cut off via the network switch 39. In this case as well the compression pressure can be adjusted via the control valve 3 as may be necessary.

I claim:

1. An apparatus for inducing bloodlessness in an extremity of a patient for a surgical procedure or for intravenous local anaesthesia, said apparatus comprising:

a source of a gas under pressure;

a compression sleeve adapted to surround said extremity and connectable with said source for pressurization thereby to compress said extremity;

a controllable pressure regulating valve between said source and said sleeve for regulation a gas pressure in said sleeve;

an automatic blood pressure measuring device for monitoring blood pressure of said patient at least intermittently and producing a signal representing measured blood pressure; and a control signal generator connected to said automatic blood pressure measuring device and to said controllable pressure regulating valve for receiving said signal representing measured blood pressure and producing a control signal operating said valve to alter pressure in said sleeve in response to a change in measured blood pressure;

a manually operated pressure control valve connected in parallel with said controllable pressure regulating valve between said source and said sleeve, and a two-way valve between said manually operated pressure control valve and said controllable pressure regulating valve for selectively controlling compression pressure in said sleeve therewith;

wherein said control signal generator operates said valve so as to maintain a compression pressure in said sleeve at a value equal to the measured blood pressure plus a predetermined additional pressure having a constant magnitude independent of the measured blood pressure; and wherein said control signal generator is integrated in a computer-supported controller provided with means for calculating said control signal from a magnitude of the measured blood pressure.

2. The apparatus defined in claim 1, further comprising a manually operated pressure control valve connected in parallel with said controllable pressure regulating valve between said source and said sleeve, and a two-way valve between said manually operated pressure control valve and said controllable pressure regulating valve for selectively controlling compression pressure in said sleeve therewith.

3. The apparatus defined in claim 2, further comprising a pressure sensor responsive to compression pressure in said sleeve and automatically enabling said manually operated pressure control valve upon said compression pressure in said sleeve as an actual value deviating from a setpoint compression pressure determined by said control signal generator from said measured blood pressure.

4. The apparatus defined in claim 3 wherein said actual value and said setpoint value are compared in said control signal generator, said control signal generator producing a signal operating said two-way valve.

5. The apparatus defined in claim 2, further comprising a pressure sensor responsive to compression pressure in said sleeve and automatically triggering an alarm upon said compression pressure in said sleeve as an actual value deviating from a setpoint compression pressure determined by said control signal generator from said measured blood pressure.

6. The apparatus defined in claim 1, further comprising a manually operated pressure control valve connected in parallel with said controllable pressure regulating valve between said source and said sleeve, and a two-way valve between said manually operated pressure control valve and said controllable pressure regulating valve for selectively controlling compression pressure in said sleeve therewith.

7. The apparatus defined in claim 6, further comprising a pressure sensor responsive to compression pressure in said sleeve and automatically enabling said manually operated pressure control valve upon said compression pressure in said sleeve as an actual value deviating from a setpoint compression pressure determined by said control signal generator from said measured blood pressure.

8. The apparatus defined in claim 7 wherein said actual value and said setpoint value are compared in said control signal generator, said control signal generator producing a signal operating said two-way valve.

9. The apparatus defined in claim 8 wherein said computer-supported controller includes displays for said measured blood pressure, said additional pressure and the setpoint value of said compression pressure, and data input means for setting said additional pressure.

10. The apparatus defined in claim 9, further comprising a manometer connected to the compression sleeve for displaying the compression pressure therein.

11. The apparatus defined in claim 6, further comprising a pressure sensor responsive to compression pressure in said sleeve and automatically triggering an alarm upon said compression pressure in said sleeve as an actual value deviating from a setpoint compression pressure determined by said control signal generator from said measured blood pressure.

* * * * *